United States Patent [19]
Palermo et al.

[11] Patent Number: 5,925,059
[45] Date of Patent: *Jul. 20, 1999

[54] DETACHABLE EMBOLIC COIL ASSEMBLY

[75] Inventors: Thomas J. Palermo, Mountain View; Son Gia, San Jose, both of Calif.

[73] Assignee: Target Therapeutics, Inc., Fremont, Calif.

[*] Notice: This patent is subject to a terminal disclaimer.

[21] Appl. No.: 08/361,330

[22] Filed: Dec. 21, 1994

Related U.S. Application Data

[63] Continuation-in-part of application No. 08/049,577, Apr. 19, 1993, abandoned.

[51] Int. Cl.$^6$ .................................................. A61M 29/00
[52] U.S. Cl. ............................................. 606/191; 606/198
[58] Field of Search ................................. 606/191, 198, 606/108, 194

[56] References Cited

U.S. PATENT DOCUMENTS

| | | |
|---|---|---|
| 3,334,629 | 8/1967 | Cohn . |
| 3,789,841 | 2/1974 | Antoshkiw . |
| 4,545,390 | 10/1985 | Leary . |
| 4,619,274 | 10/1986 | Morrison . |
| 4,739,768 | 4/1988 | Engelson et al. . |
| 4,781,177 | 11/1988 | Lebigot . |
| 4,813,934 | 3/1989 | Engelson et al. . |
| 4,832,055 | 5/1989 | Palestrant . |
| 4,884,579 | 12/1989 | Engelson . |
| 4,957,501 | 9/1990 | Lahille et al. . |
| 4,994,069 | 2/1991 | Ritchart et al. . |
| 5,002,556 | 3/1991 | Ishida et al. . |
| 5,062,829 | 11/1991 | Pryor et al. . |
| 5,064,434 | 11/1991 | Haber . |
| 5,098,440 | 3/1992 | Hillstead . |
| 5,108,407 | 4/1992 | Geremia et al. . |
| 5,109,867 | 5/1992 | Twyford, Jr. . |
| 5,122,136 | 6/1992 | Guglielmi et al. . |
| 5,133,731 | 7/1992 | Butler et al. . |
| 5,167,624 | 12/1992 | Butler et al. . |
| 5,174,276 | 12/1992 | Cockard . |
| 5,192,301 | 3/1993 | Kamiya et al. . |
| 5,217,484 | 6/1993 | Marks . |
| 5,234,437 | 8/1993 | Sepetka . |
| 5,250,071 | 10/1993 | Palermo ................................. 606/198 |
| 5,261,916 | 11/1993 | Engelson ................................ 606/191 |
| 5,263,964 | 11/1993 | Purdy . |
| 5,304,195 | 4/1994 | Twyford, Jr. et al. . |
| 5,312,415 | 5/1994 | Palermo . |
| 5,601,600 | 2/1997 | Ton ....................................... 606/191 |

FOREIGN PATENT DOCUMENTS

0341039  11/1989  European Pat. Off. .

*Primary Examiner*—Michael Buiz
*Assistant Examiner*—Kevin Truong
*Attorney, Agent, or Firm*—Morrison & Foerster LLP

[57] ABSTRACT

This invention is a surgical instrument and specifically is a device for delivering embolic coils to a selected site within the vasculature of a human body via use of a catheter. The invention further includes the coils. In particular, the device uses embolic coils having interlocking ends, e.g., clasps or hooks, on the ends of the coils. The coils may further be secured to each other by a control wire within the catheter. Retraction of the optional control wire into the catheter body uncouples the distal coil.

14 Claims, 8 Drawing Sheets

DETACHABLE EMBOLIC COIL ASSEMBLY

RELATED APPLICATIONS

This is a continuation-in-part of U.S. patent application Ser. No. 08/049,577, filed Apr. 19, 1993, now abandoned entitled "Detachable Embolic Coil Assembly Using Interlocking Hooks and Slots," the entirety of which are incorporated by reference.

FIELD OF THE INVENTION

This invention is a surgical instrument and specifically is a device for delivering embolic coils to a selected site within the vasculature or other lumen of a human body via use of a catheter. The invention further includes the coils. In particular, the device (typically a "pusher assembly" in conjunction with a catheter) uses embolic coils having interlocking ends, e.g., clasps or hooks, on at least one end of the coils. The coils may further be secured to each other by a control wire within the catheter. The coils are pushed out the end of the catheter for placement and retraction of the optional control wire into the catheter body uncouples the distal coil. If no control wire is used, the coil is self-disengaging.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in U.S. patent application Ser. No. 07/806,898 ("Detachable Pusher-Vasoocclusive Coil Assembly with Threaded Coupling") and Ser. No. 07/806,912 ("Detachable Pusher-Vasoocclusive Coil Assembly with Interlocking Ball and Keyway Coupling"). These show methods and devices for delivery of coils or wires within the human body to sites such as aneurysms, to occlude those sites. Coils such as are discussed in U.S. Pat. No. 4,994,069, may be of a regular or helical configuration or assume a random convoluted configuration at the selected site. The coils normally are made of a radiopaque, biocompatible metal such as platinum, gold, tungsten, or alloys of these and other metals.

In treating aneurysms it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the distal end of a catheter. In treating peripheral or neural conditions requiring occlusion, the sites are accessed with flexible, small diameter catheters such as those shown in U.S. Pat. Nos. 4,739,768 and 4,813,934. The catheter may be guided to the site through the use of guidewires (see U.S. Pat. No. 4,884,579) or by flow-directed means such as balloons placed at the distal end of the catheter. Use of guidewires involves the placement of relatively long, torqueable proximal wire sections within the catheter, which proximal sections are attached to more flexible distal end wire section designed to be advanced across sharp bends at vessel junctions. The guidewire is visible using x-ray and allows a catheter to be manipulated through extremely tortuous vessels, even when such vessels are surrounded by soft tissue such as the brain.

Once the selected site has been reached, the catheter lumen is cleared by removing the guidewire (if a guidewire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the pusher into the vascular site. This technique of discharging the coil from the distal end of the catheter has a number of undesirable limitations. First, because of the plunging action of the pusher and the coil, the positioning of the coil at the site cannot be controlled to a fine degree of accuracy. Second, once the coil has left the catheter, it is difficult to reposition or retrieve the coil if such is desired. Nevertheless, the technique has the benefit of delivering multiple coils at low cost with a short delivery time.

Several techniques have been developed to enable more accurate placement of coils within a vessel. In one technique (U.S. Pat. No. 5,122,136, issued Jun. 16, 1992) the coil is bonded via a metal-to-metal joint to the distal end of the pusher. The pusher and coil are made of dissimilar metals. The coil-carrying pusher is advanced through the catheter to the site and a low electrical current is passed through the pusher-coil assembly. The current causes the joint between the pusher and the coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a period of time so that rapid detachment of the coil from the pusher does not occur.

Another technique for detaching an embolic coil shown in U.S. patent application No. 07/806,912. In that document, a coil having an enlarged portion is mated with a pusher having a keyway adapted to receive the enlarged portion of the coil in an interlocking relationship is covered by a coaxial member about the pusher and the coil. The coaxial member is movable by sliding the member axially. As the coaxial member is moved away from the junction where the coil's member engages the member of the keyway of the pusher, the coil disengages and the pusher is removed.

Another device for placement of coils is shown in U.S. patent application No. 07/806,898. This device includes a coil having a helical portion at one end and a pusher which is threaded to the inside of the helical coil by the use of a threaded section on the outside of the pusher. The device operates to release the coil by engaging the proximal end of the coil with a sleeve while the pusher is unthreaded. Once the pusher is free, the sleeve may be used to push the coil out into the treatment area.

Another method of placing an embolic coil is shown in U.S. Pat. No. 5,108,407. This patent shows the use of a device in which embolic coils are separated from the distal end of a catheter by the use of heat-releasable adhesive bonds. The coil adheres to the therapeutic device via a mounting connection using a heat sensitive adhesive. Laser energy is transferred through a fiber optic cable, which cable terminates at the connector. The connector becomes warm and releases the adhesive bond between the connector and the coil.

None of these disclosed devices suggest coils having interlocking ends which allow an embolic coil to be positioned within a vessel and then released upon ejection of the coil from the catheter distal end or, optionally, upon retraction of a control wire positioned within that interlocking end.

SUMMARY OF THE INVENTION

This invention is a device for placing detachable coils within the vasculature of the human body so to occlude that site with the coils. The device includes a coil that carries an interlocking connector or end such as a slot, hook, or clasp at at least one end of the coil, preferably at its proximal end. The device includes a pusher (positioned within the catheter) which has a cooperating connector at its distal end which interlocks with the connector or end situated on the coil. The coils may have interlocking clasps at each end thereby allowing a number of coils to be strung together and yet individually released. The coil may alternatively carry a receiving slot on at least one end of the coil adapted to cooperatively receive a hook which is shaped to engage the receiving slot. The coil having such a receiving slot may also have such a hook at the end of the coil distant from the receiving slot. An optional control wire passing through the catheter, the pusher assembly, the pusher clasp, and the coil ends releases the coil as the control wire is retracted through axial passageways or openings provided in the two clasps.

Another portion of the invention is a method for occluding a selected vascular site comprising the steps of: (a) accessing the site with a distal end of a catheter; (b) advancing the assembly described above through the catheter with the coil interlocked with the pusher to a position out the end of the distal end of the catheter; (c) disengaging the coil optionally by withdrawing the control wire from the coil; and (d) withdrawing the catheter and pusher from the vessel.

DESCRIPTION OF THE INVENTION

The coil assembly (100) is shown in FIG. 1. The coil (102) is shown as helical in form, although it may be any other suitable form. The coil should be of a size sufficiently small that it may be advanced through a catheter that is appropriately sized for accessing the targeted vascular site. For instance, when accessing a brain aneurysm in a small vessel, an appropriately sized catheter is quite small and very flexible. The coil in such a situation must be small enough to fit through the catheter and out its distal end at the treatment site.

The coil is desirably made up of a radiopaque, physiologically compatible material. For instance, the material may be platinum, gold, tungsten, or alloys of these. Certain polymers are also suitable as coil material either alone or in conjunction with metallic markers providing radiopacity. These materials are chosen so that the procedure of locating coils within the vessel may be viewed using radiography. However, it is also contemplated that these coils may be made of various other biologically inert polymers or of carbon fiber.

The size of the coil and its constituent winding will depend upon the use to which the coil will be placed. For occluding peripheral or neural sites, the coils will typically be made of 0.05 to 0.15 mm diameter wire (platinum or platinum/tungsten alloy) that may be wound to have an inner diameter of 0.15 to 1.5 mm with a minimum pitch—that is to say that the pitch is equal to the diameter of the wire used in the coil. The outer diameter is then typically between 0.25 mm to 1.8 mm. The length of the coil will normally be in the range of 0.5 to 60 cm, preferably 0.5 to 40 cm.

If desired, the coil may be formed in such a way that the coil is essentially linear as it passes through the catheter and yet assumes a randomly oriented relaxed condition after it is released from the distal end of the catheter. A discussion of this variation may be found in U.S. Pat. No. 4,994,069.

Figure 1A:
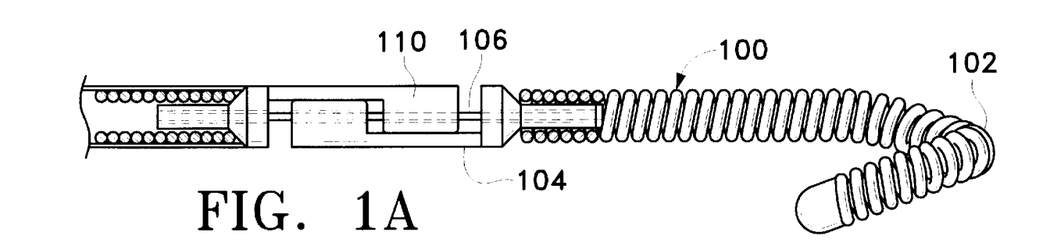
FIGS. 1A and 1B show, respectively, a partial sectional view of a pusher assembly and an engaged coil assembly having an interlocking clasp at only one end and a front three-quarters view of one variation of the interlocking clamp.
Figure 1B:
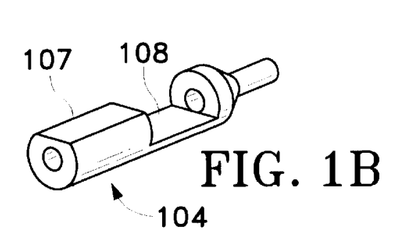

Fixedly attached to coil (102), as is shown in FIG. 1A, is interlocking clasp (104). Interlocking clasp (104) as is depicted in the front three-quarter view in FIG. 1B, has an interior passageway allowing the control wire (106) to pass completely therethrough. As is shown in FIG. 1A, the male portion of the next adjacent interlocking clasp (110) fits into the area (108) left within clasp (104) so to allow the interlocking to take place. Said another way, the distal portion of interlocking clasp (104) is generally cylindrical in shape but has a surface (107), which may be cut or milled away, allowing the portion to mesh within the middle area (108) of an adjacent clasp. The proximal section is adapted for attaching to a coil or to a pusher assembly. The attachment may be by welding, soldering, gluing, or the like. With a control wire (106) passing through the axis of both interlocking clasps (104) and (110), the two are locked together. As is shown in FIG. 1A, the control wire may extend through the length of coil (102).

Figures 2, 3:
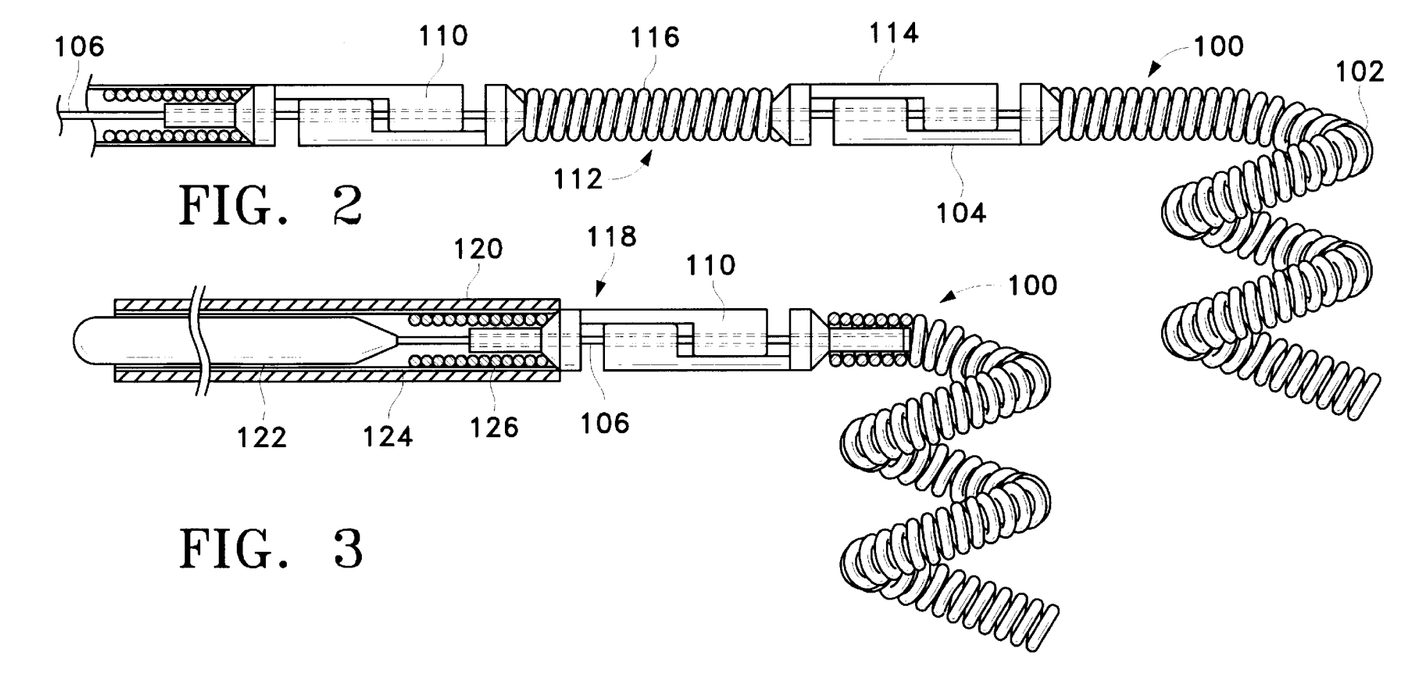
FIG. 2 shows a series of coil assemblies having either one or two interlocking clasps at their ends.
FIG. 3 shows deployment of the interlocking coil within a catheter.

FIG. 2 shows an intermediate coil assembly (100) comprising coil (102) and interlocking clasp (104) (joined with coil assembly (112)) which has interlocking clasp (114) fixedly attached at both ends of the intervening coil (116). As was the situation in FIG. 1A, the proximal interlocking clasp (114) is joined by control wire (106) with interlocking clasp (110). In this way, a significant number of coils (112) may be loaded onto a control wire (106) and delivered to the treatment site without removal of the control wire from the catheter.

FIG. 3 shows the relationship of coil assembly (100) and the pusher assembly (118) with its distal interlocking clasp (110) as it fits within catheter sheath (120). Also shown is movable inner core member (122) and the sheath (124) which fits within catheter sheath (120,) and supports interlocking clasp (110). Shown in FIG. 3 is the stiffener spring (126) which provides form and support for the distal end of the pusher assembly (118) and in particular rigidly adheres to interlocking clasp (110). Inner core member (122) allows the control wire (106) to be moved axially along the interior of the catheter sheath (120) and the pusher assembly (118). Movement of the inner core member (122) in a proximal direction permits uncoupling of the coil as will be discussed in more detail below.

The length of pusher assembly (118) will be such as to be capable of being advanced entirely through the catheter to place coil (102) at the target site but yet with a sufficient portion of the proximal end of the pusher assembly (118) protruding from the proximal end of the catheter to enable the control wire (106) to be manipulated. For use in peripheral or neural surgeries, the pusher will normally about 100–200 cm in length, more normally 130–180 cm in length. The diameter of the pusher assembly (118) is usually in the range of 0.25 to about 0.90 mm.

As indicated previously, conventional catheter insertion and navigational techniques involving guidewires or flow-directed devices may be used to access the site with a catheter. Once the distal end of the catheter is positioned at the site, often by locating its distal end through the use of radiopaque marker material and radiography, the catheter is cleared. For instance, if a guidewire has been used to position the catheter, it is withdrawn from the catheter and then the pusher assembly (118) having coil assembly (100) at the distal end is advanced through the catheter. The pusher assembly (118) is advanced past the distal end of the catheter so that the coil is free of the catheter and with the coil positioned precisely at the desired treatment site.

Figure 4:
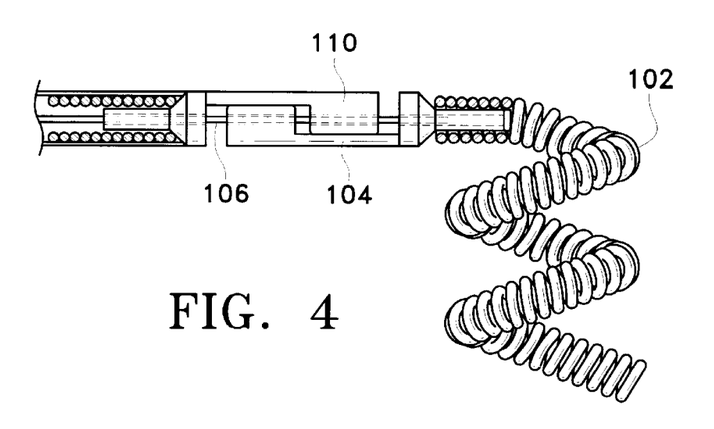
FIGS. 4 and 5 show the operation of the assembly as it places a coil within a target site.
Figure 5:
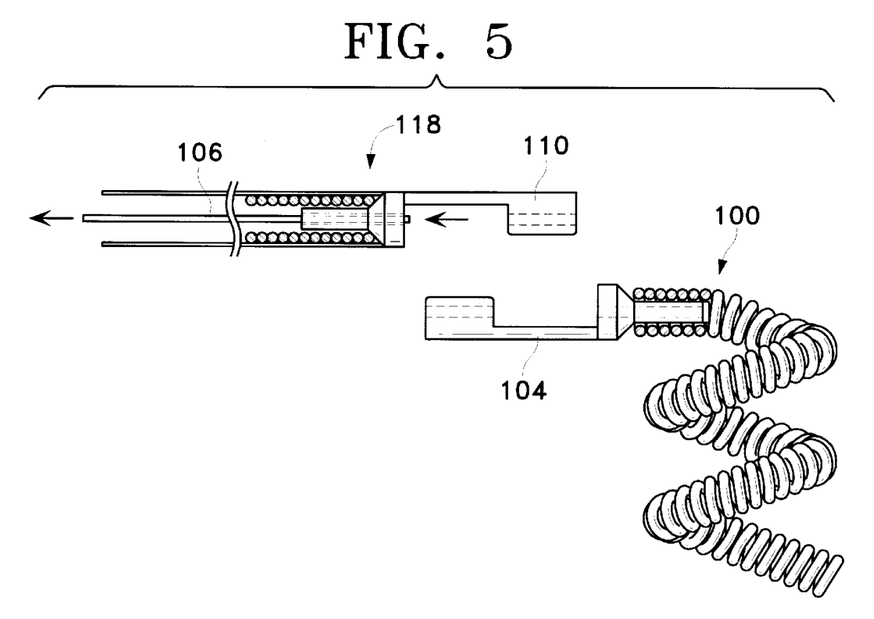

As is shown in FIGS. 4 and 5, control wire (106) is withdrawn from the junction between coil interlocking clasp (104) and the other interlocking clasp (110). Coil assembly (100) is then free. The entire catheter may then be removed or the pusher assembly (118) may be withdrawn from the catheter lumen to provide for installation of other coils. If additional coils are to be placed at the target site, the procedure is repeated. After the desired number of coils have been placed at the site, the catheter is withdrawn from the vessel.

Figure 6A:
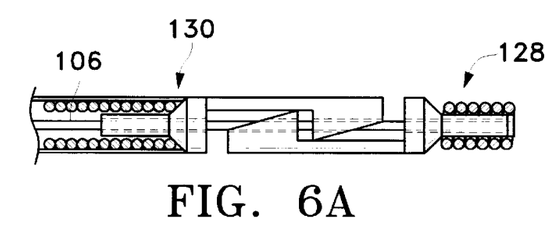
FIGS. 6A and 6B show, respectively, a partial sectional view of a pusher assembly and an engaged coil assembly having a variation of an interlocking clasp and a front three-quarter view of that variation of the interlocking clasp.

FIG. 6A shows a variation in which coil assembly (128) is interlocked with pusher assembly (130) by control wire (106). The depicted coil assembly (128) and pusher assembly (130) are different in that they incorporate the interlocking clasp (132) design shown more clearly in FIG. 6B. The interlocking clasp (132), as with the clasp depicted in FIG. 1B, utilizes an open area (134) within the clasp (132) to accept the mating ramp latch (136) from another similar clasp. The ramp latch (136) typically has a slot (138) and a passageway (140) to permit passage of the control wire through the clasp (132) from end to end without obstruction.

Figure 6B:
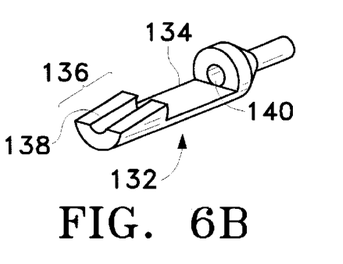

The ramp latch (136) allows easy assembly of a string of coils within the catheter for subsequent placement using the device.

Figure 7A:
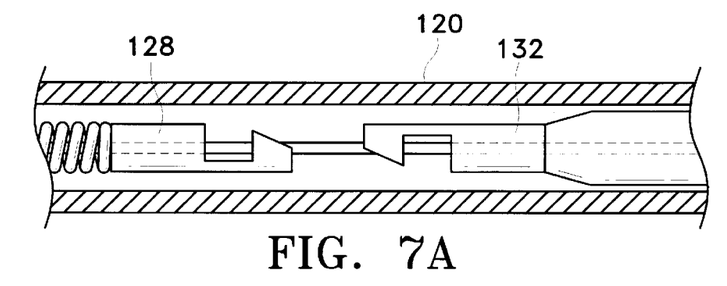
FIGS. 7A, 7B, and 7C show a method of attaching coils having the interlocking clasp shown in FIGS. 6A and 6B to a pusher body within the catheter lumen.
Figure 7B:
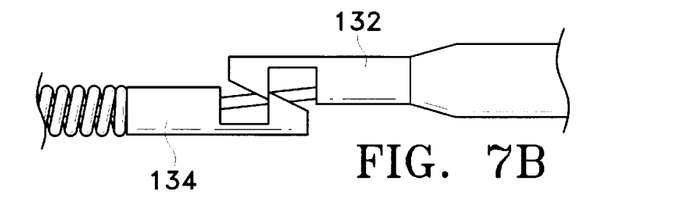
Figure 7C:
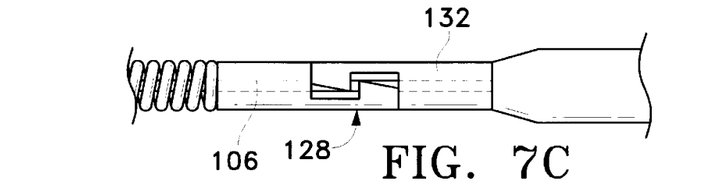

Such an assembly process is shown in FIGS. 7A, 7B, and 7C.

FIG. 7A shows a pusher assembly approaching a coil assembly (128) which has been previously placed within a catheter sheath (120). The distal interlocking clasp (132) on the pusher assembly is positioned to interlock with the proximal interlocking clasp (134) on the coil assembly (128).

FIG. 7B shows the two interlocking clasps (132 and 134) as they approach their respective ramps contacting and causing the two clasps to displace axially within the catheter sheath.

FIG. 7C shows the location of the coil assembly (128) and the pusher assembly (132) after the respective clasps are interlocked and the control wire (106) has been placed through the passageways within the clasps.

Figure 8:
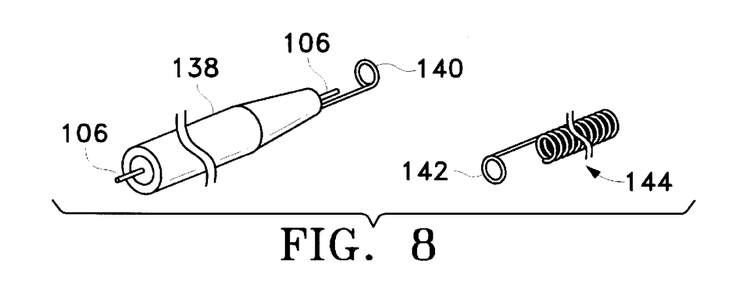
FIG. 8 shows a variation of the invention in which both the coils and the pusher body have simple loops as interlocking clasps.

FIG. 8 shows an elegantly simple variation of the invention in which the pusher (138) is a tubing member having a control wire (106) within its core. The clasp portion (140) is a simple loop comprising, e.g., wire or small rod. The corresponding interlocking loop (142) on the coil (144) forms the junction with the clasp on the pusher.

The variation of the invention shown in FIGS. 6A, 6B, 7A, 7B, 7C, and 8 may be placed within the vasculature in the same manner as shown for the variation shown in FIGS. 4 and 5.

Figure 9A:
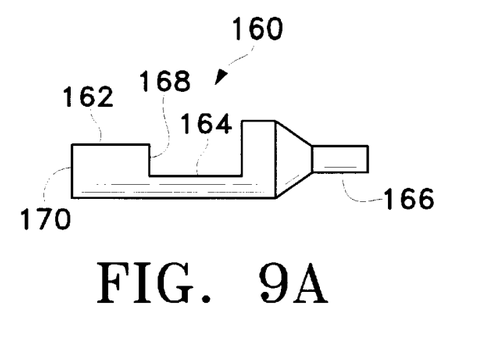
FIG. 9A shows a side view of a clasp, joinable to a coil or pusher, similar in shape to the FIG. 1A to 5 clasp but, in design without, without the control wire.
Figure 11:
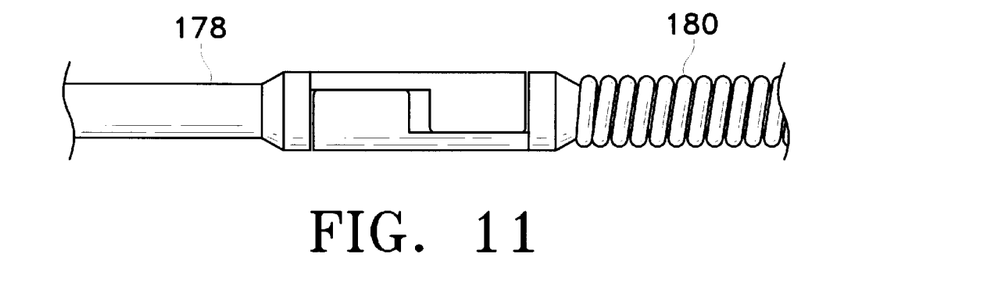
FIG. 11 shows the FIG. 9A clasp mounted on a pusher and on a coil as would be seen in a catheter.

FIG. 9A shows a side view of a clasp (160) similar in design to the clasp discussed in conjunction with FIGS. 1A, 1B, 2, 3, 4, and 5. In contrast to the clasp found on those vasoocclusive devices, the FIG. 9A clasp (160) contains no lumen therethrough for a control wire. As was the case with the clasp above, the clasp is generally cylindrical in shape but has a surface (162) which may be cut or milled away to allow the to mesh with a receiver area (164) in the next adjacent clasp as is shown in FIG. 11. The other end of the clasp is adapted to allow joining with the end of a coil or pusher. Although that other end is shown with a reduced diameter (166), to allow insertion of the end (166) into the coil or pusher, other end shapes are certainly appropriate, e.g., helical to accept the coil, square, bulbed, etc., the reduced diameter cylinder is very desirable. The vertical or mating surface (168) pulls the next device in the chain along when it contacts the similar surface in that next device. The end surface (170) pushes against the next device when in a chain.

Figure 9B:
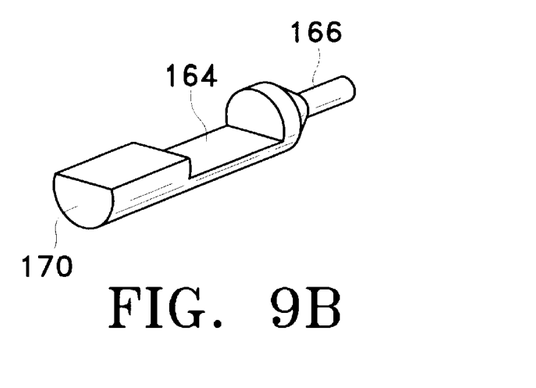
FIG. 9B shows a front three-quarter view of the FIG. 9A clasp.

FIG. 9B shows a front, elevated, three-quarter view of the clasp found in FIG. 9A. FIG. 9B shows the end surface (170), the receiver area (164), and the reduced diameter shaft (166) for mating with the coil or pusher.

Figure 10A:
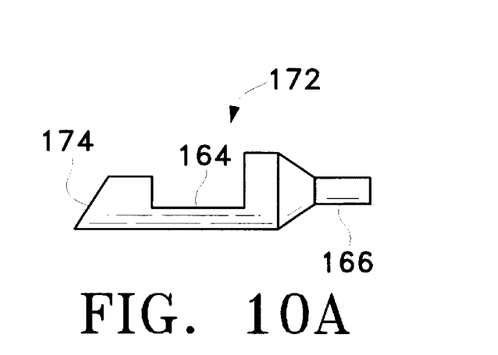
FIG. 10A shows a side view of a clasp similar to the clasp shown in FIGS. 9A and 9B but with a ramped end.

FIG. 10A shows a clasp (172) much like that shown in FIG. 9A except that the end surface is a ramp (174) to permit assembly ease in placing the coils in the catheter or introducer.

Figure 10B:
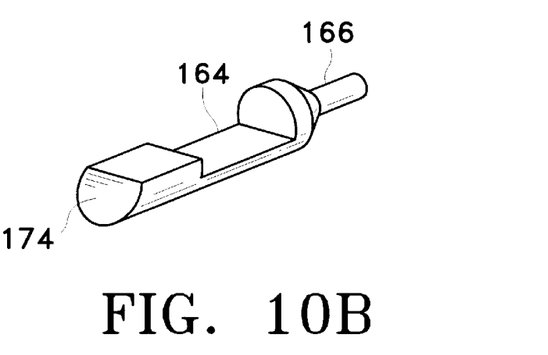
FIG. 10B shows a front three-quarter view of the FIG. 10A clasp.

FIG. 10B shows a front, elevated, three-quarter view of the clasp found in FIG. 10A. FIG. 10B shows the end ramp (174), the receiver area (164), and the reduced diameter shaft (166) for mating with the coil or pusher.

FIG. 11 shows how the clasps found in FIGS. 9A and 9B mesh when installed on a pusher (178) or a coil (180). It is within the scope of this variation of the invention that the clasp be mounted on the ends of pushers, coils (one or both ends), and that multiple coils or other vasoocclusive devices be joined in multiple end-to-end trains for introduction into the vasculature.

Figure 12:
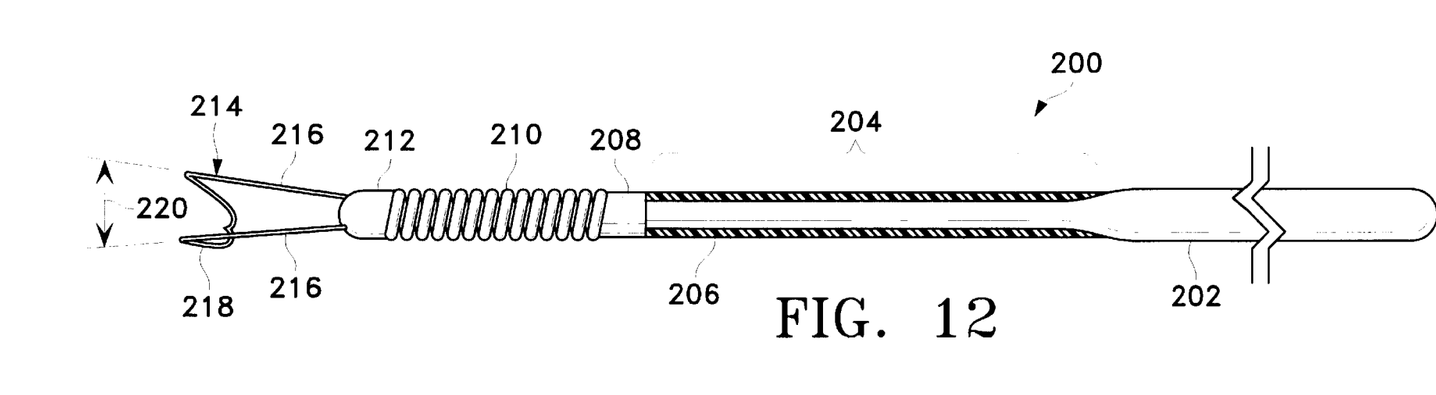
FIG. 12 shows in partial cross-sectional view, a guidewire pusher assembly having a W-shaped hook at the distal end for engaging coils having a cooperatively shaped slot.

An additional variation of the pusher assembly (200) is shown in FIG. 12. The configuration of the body of the pusher assembly (200) is not particularly critical, and many variations known in the art would likely be suitable. The variation shown here entails, at the distal end, a stainless steel core (202) having a small diameter section (204) covered by a desired polymeric material (206) such as tetrafluoroethylene, or other suitable fluorinated hydrocarbon polymers; hydrophilic polymers such as polyvinylpyrrolidone, polyethyleneoxide, or polyhydroxyethylmethacrylate, or copolymers, or mixtures, or blends thereof; or various silicone-based polymeric materials; or polyolefins such as polyethylene, polypropylene, or their copolymers, mixtures, or blends; or appropriate polyurethane polymers. This coating provides a slippery surface allowing ease of insertion and traverse through the catheter body.

It is desirable to include a radiopaque marker (208). Such markers are common in this art and may be made of known radiopaque materials such as platinum, palladium, or other such materials. Commonly, the radiopaque marker (208) is a coil which is brazed or soldered to the guidewire and may be coated with the polymeric materials (206). This marker allows the tending physician to monitor the progress of the guidewire tip via fluoroscopy and, obviously, allow proper placement of the coil which is attached to the end of the pusher guidewire (200).

More distal of the radiopaque marker (208) may be found a flexible coil (210). This coil covers a tapered section of the core wire (202). Tapering the inner wire and enclosing it in a wire coil increases the column strength of the tapered wire section without significant loss of flexibility and increases the radial capacity of the guidewire to allow fine manipulation of the guidewire through various tortuous portions of the vasculature. The tip of the core wire (202) and the distal portion of the wire coil (210) are typically joined by use of a solder joint (212). To this point, the guidewire is of a typical guidewire respected in this art. See, for instance, those guidewires shown in U.S. Pat. Nos. 3,789,841; 4,545,390; and 4,619,274.

Unique to this variation of the invention is the hook (214) placed at the most distal end of the guidewire assembly (200) which transforms it into a pusher.

Engaging hook (214) has two legs (216) which are based in solder joint (212). The outer hook portion (218) is configured so that it slides into the conforming slot in the coils as discussed below. The diameter (220) of the hook (214) is typically no larger than the inside diameter of the catheter assembly into which it is placed. Obviously, if the diameter is larger, it will bind in the catheter and be of little use. The most distal portion of the hook (218) is configured in such a way that the "W" portion is in a plane which is generally perpendicular to the longitudinal axis of the guidewire pusher assembly (200). The engaging hook (214) need be made only of a material which is adequate under the circumstances of use. For instance, the hook may be of a stainless steel wire which may be soldered onto the end of the guidewire assembly (200) and bent into desirable shape. In this way, the hook may be used to push the attached coil through the catheter without bending. The length of guidewire pusher assembly (200) should be such as to be capable of being advanced entirely through a catheter to place a coil such as discussed below at the target site, but yet retain a sufficient portion of the proximal end of the guidewire pusher assembly (200) protruding from the proximal end of the catheter to enable the pusher to be manipulated. For use in peripheral and neural surgeries, the pusher will normally be about 100–200 cm in length, more normally 130–180 cm in length. The diameter of the guidewire pusher assembly (100) is usually in the range of 0.25 to about 0.90 mm.

Figure 13:
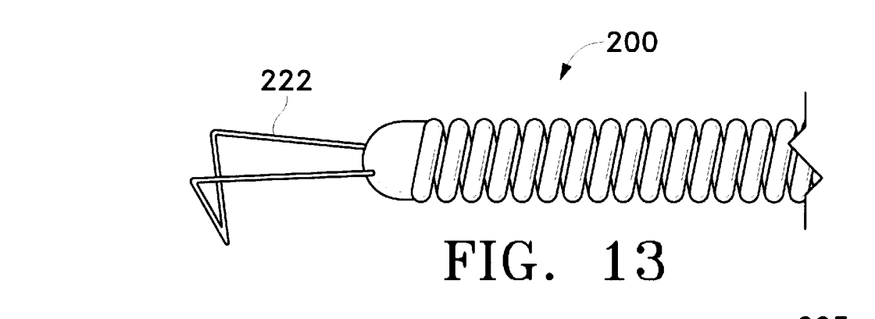
FIG. 13 shows the distal tip of a variation of the guidewire pusher shown in FIG. 12 but having a simply V-shaped hook positioned at the distal end.
Figure 14:
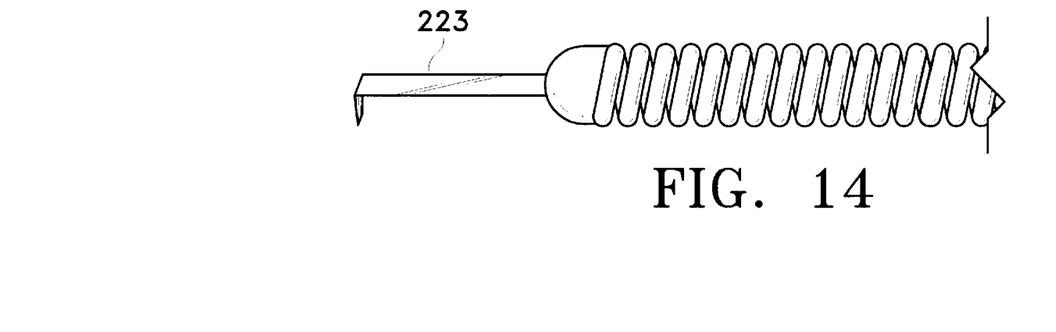
FIG. 14 shows the distal tip of a variation of the guidewire pusher shown in FIG. 12 but having a solid hook positioned at the distal end.

FIG. 13 shows a variation of the distal tip of guidewire pusher assembly (200) having a slightly different configuration than that shown in FIG. 12. In this instance, the hook is a simple "V"- or "U"-shaped hook which also will engage with the slotted coils described below. The materials of construction and other such variables are similar to those for the hook of FIG. 12. FIG. 14 shows an additional variation of the pusher assembly (200) having a hooked distal tip. This hook (223) is of a bent ribbon rather than the wire configuration shown in FIGS. 12 and 13. The materials of construction and method of attachment are similar to those used in the FIGS. 12 and 13 variations. The ribbon is bent in such a way as to allow insertion of the hook's bent lip into the slot found in the coils discussed below.

Figure 15:
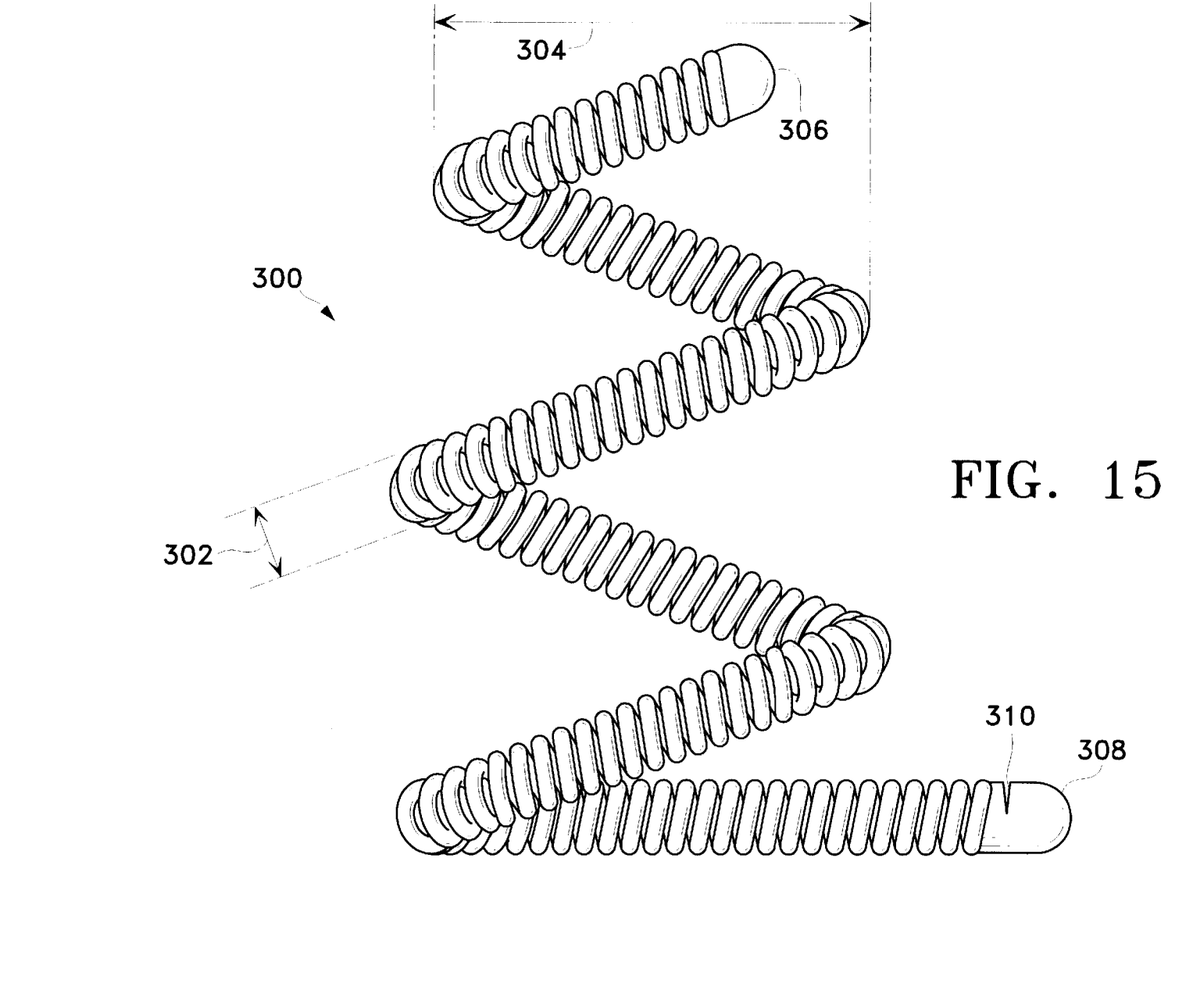
FIG. 15 shows an embolic coil having the desired engaging slot at one end.

The coil typical of that which might be used with this invention, is shown in FIG. 15. The coil (300) is shown as helical in form, although it may be any other suitable form. The coil shown is one having a primary and a secondary diameter. The primary diameter (302) is sufficiently small that the coil (300), when straightened, would fit inside the lumen of the catheter assembly. The coil assembly shown assumes a second diameter (304) when ejected from the tip of the catheter using the pusher guidewire (200) shown in FIG. 12.

Coil (300) may be made up of the same or similar radiopaque, physiologically compatible materials discussed in relation to coil (100) applicable to FIGS. 1–5 above. The size, length, diameter (inner and outer), pitch, and configuration all may be as discussed above.

Whatever the configuration may be, the coil typically has caps at each end. Specifically, the distal end of the coil (300) will have a distal cap to (306) which may be solder or epoxy or other filling adhesive or fused from the coil metal, preferably forming a rounded form to prevent the coil from hanging up within the catheter or an inappropriate place within the patient's vasculature. The unique aspect of this invention is found at the proximal end of the coil (308). The proximal end typically will be soldered or glued, much in the way that the distal end has been, but is configured in such a way that a slot (310) is opened during the soldering or gluing process and will accept the hook, variously (214) in FIG. 12 or (222) in FIG. 13 or (223) in FIG. 14 into the slot. Obviously, the receiving slot (310) may be generally substantially perpendicular to the local axis of the coil.

Figure 16:
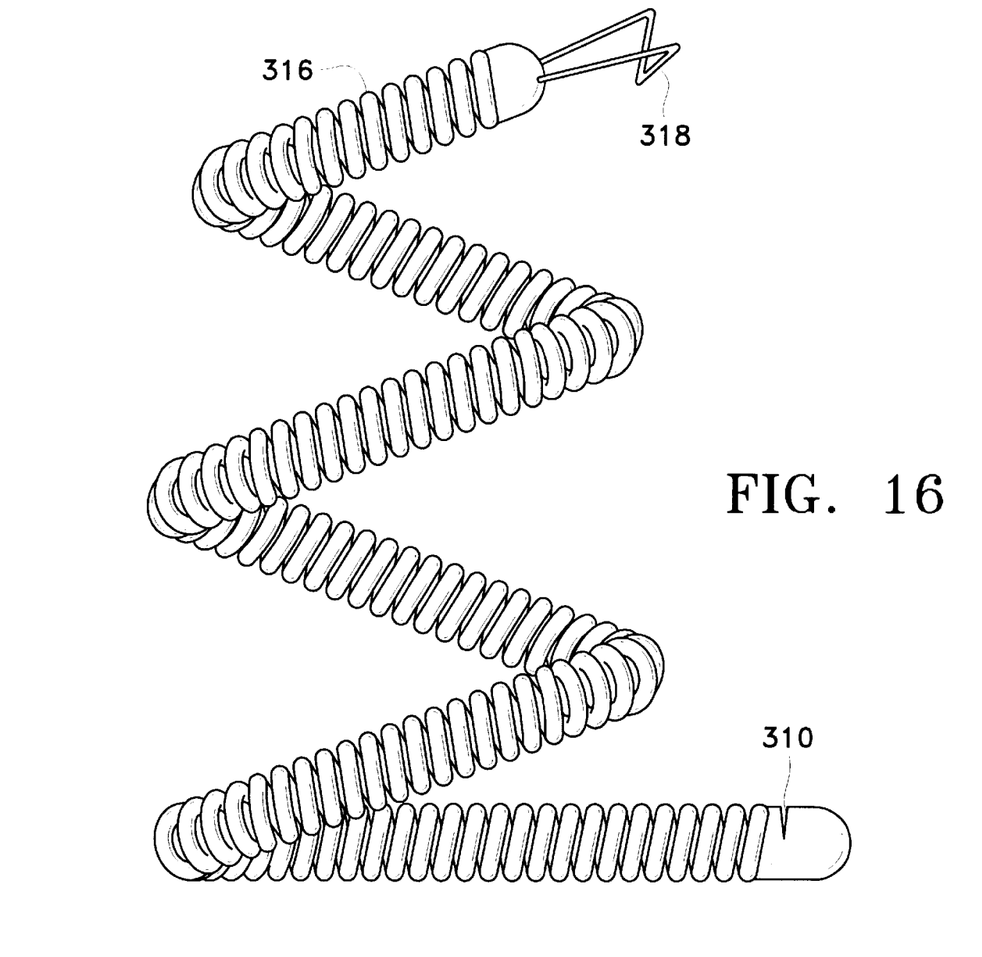
FIG. 16 shows a coil similar in construction to that found in FIG. 15, but also having a hook at its other end.

FIG. 16 depicts a variation of the coil shown in FIG. 15. This variation, however, includes, at the distal end of the coil (316), a hook (318) of configuration similar to that found in discussing the guidewire pusher assemblies in FIGS. 12 and 13. This configuration allows the introduction of discrete segments of coils into the catheter and separate placement of them should such a situation be desirable. In such an instance, the hook (318) would be introduced into the receiver slot (310) in the similar coil next in line. The most proximal of the coils would, in turn, be engaged with a hook on a pusher assembly such as (200) shown in FIG. 12.

Figure 17:
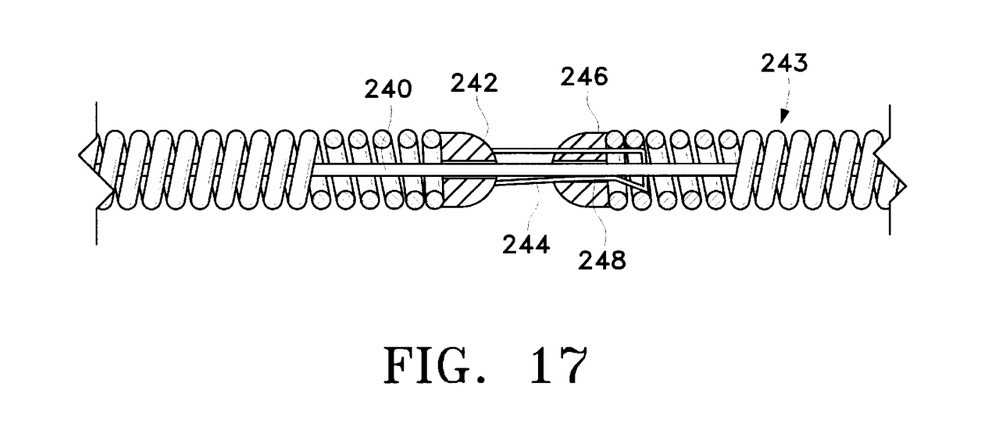
FIG. 17 shows an embolic coil similar to that in FIG. 15 and a pusher similar to FIG. 14 using a control wire to allow disengagement of the coil.

FIG. 17 shows a variation of the invention shown in FIGS. 12–16 in which a control wire (240) is placed generally through an axial passageway between the distal (or proximal) end (242) of a coil or pusher having a hook (244) and the corresponding end (246) of a coil (243) having a slot (248) cooperating with the hook (244). As with the variation shown in FIGS. 1–8, the control wire (240) may be withdrawn when the coil (243) is situated at the selected vascular site to disengage the coil (243). Use of the control wire permits more precise placement of coil (243) and its gentle disengagement.

Figure 18:
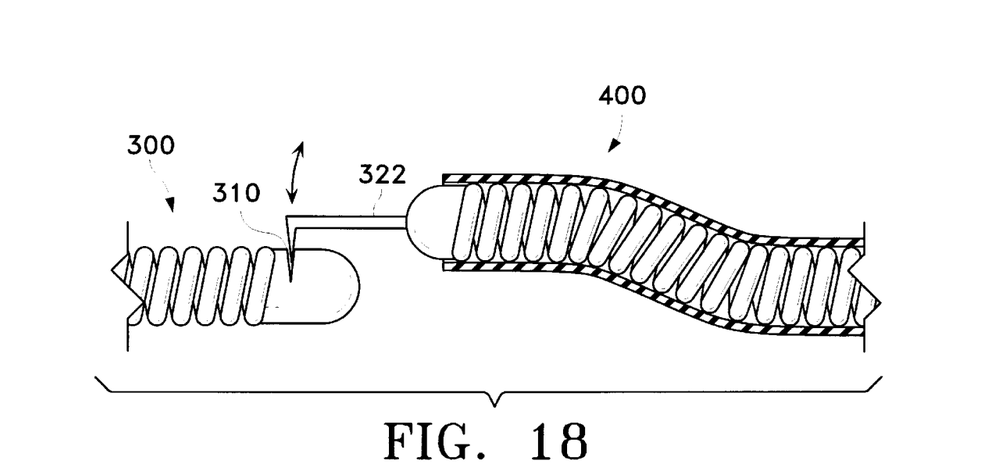
FIG. 18 depicts the manner in which the invention operates.

FIG. 18 is a side view depicting how the hook (322), as depicted here, is placed in slot (310) of the coil assembly (300). The tip of a typical catheter (400) is shown in the Figure. Again, the overall diameter of the various assemblies as put together for introduction into or out of catheter must be of a diameter smaller than the diameter lumen in catheter (400). Obviously, too large a coil/pusher combination will not be particularly valuable in a situation where such is needed.

As indicated previously, conventional catheter insertion and navigational techniques involving guidewires or even flow-directed devices may be used to access a chosen vascular site with a catheter. Once the distal end of the catheter is positioned at that chosen site, often by locating its distal end through the use of a radiopaque marker material and radiography, the catheter is cleared. For instance, if a guidewire has been used to position a catheter, it is withdrawn from the catheter and then the guidewire pusher assembly such as (200) shown in FIG. 12 having coil assembly such as (300) in FIG. 15 is assembled and introduced into the proximal end of the catheter. The guidewire pusher assembly is then advanced so that its distal end is free of the distal end of the catheter and the coil positioned precisely at the desired site. The pusher assembly (200) may require a twisting movement to free the distal hook from the receiving slot in the coil.

Modifications of the device described above and methods of using it in keeping with this invention that are apparent to those having skill in this mechanical and surgical instrument design art and related fields are intended to be within the scope of the claims which follow.

I claim:

1. A detachable coil assembly for use in occluding a selected site within a vessel comprising a coil with opposing ends on a coil axis and having, on at least one end, a solid, interlocking, shaped clasp having no axial passageway therethrough and having an axis generally colinear with the coil axis, said interlocking clasp configured to interlock with a similar solid, interlocking, shaped clasp having no axial passageway therethrough.

2. The assembly of claim 1 where the coil is a helical coil.

3. The assembly of claim 2 where the coil has a random or straight configuration.

4. The assembly of claim 1 where the coil assembly has said solid interlocking shaped clasps at each of the coil ends.

5. The assembly of claim 1 in which the interlocking clasp comprises a distal portion of a generally cylindrical shape, a middle portion adapted to accept said cylindrical distal portion from a similar interlocking clasp, and a proximal section adapted for attaching to the coil.

6. The assembly of claim 1 in which the interlocking clasp comprises a generally cylindrical distal portion having a ramp adapted to engage a ramp on a similar interlocking clasp, a middle portion adapted to accept a cylindrical portion with a ramp or a similar interlocking clasp, and a proximal portion adapted for attaching to the coil.

7. The assembly of claim 1 additionally comprising one or more coil assemblies.

8. A combination pusher assembly-coil assembly for use in occluding a selected site within a vessel comprising:

(a) a coil with opposing ends on a coil axis and having, on at least one end, a solid, interlocking, shaped clasp having no axial passageway therethrough and having an axis generally colinear with the coil axis, said interlocking clasp configured to interlock with a similar solid, interlocking, shaped clasp having no axial passageway therethrough; and (b) a pusher assembly comprising a tubular pusher sheath having a proximal end and a distal end and adapted to fit within a catheter sheath, and said similar solid, interlocking, shaped clasp having no axial passageway therethrough, said similar clasp located at the distal end of the pusher sheath, said similar clasp connected to the distal end of the pusher assembly.

9. The assembly of claim 8 where the coil is a helical coil.

10. The assembly of claim 9 where the coil has a straight or random configuration.

11. The assembly of claim 8 additionally comprising a catheter sheath disposed about the pusher sheath.

12. The assembly of claim 8 additionally comprising more than one coil.

13. The assembly of claim 8 in which the interlocking clasps comprise a distal portion of a generally cylindrical shape, but having a middle portion adapted to accept said cylindrical distal portion from a similar clasp to allow interlocking with said similar clasp, and a proximal section adapted for attaching to the coil.

14. The assembly of claim 8 in which the interlocking clasps comprise a generally cylindrical distal portion having a ramp adapted to engage a ramp of a similar interlocking clasp, a middle portion adapted to accept a cylindrical portion with a ramp or a similar interlocking clasp, and a proximal portion adapted for attaching to the coil.

* * * * *